(12) United States Patent
Schonert et al.

(10) Patent No.: US 6,506,501 B1
(45) Date of Patent: Jan. 14, 2003

(54) FOIL FOR WRAPPING HAIR ENDS

(75) Inventors: Dieter Schonert, Reinheim (DE);
Gerhard Maresch, Darmstadt (DE);
Gernot Mecks, Hoechst/Odw. (DE)

(73) Assignee: Wella AG, Darmstadt (DE)

( * ) Notice: Subject to any disclaimer, the term of this patent is extended or adjusted under 35 U.S.C. 154(b) by 0 days.

(21) Appl. No.: 09/355,656

(22) PCT Filed: Oct. 31, 1998

(86) PCT No.: PCT/EP98/06905

§ 371 (c)(1),
(2), (4) Date: Sep. 27, 2001

(87) PCT Pub. No.: WO99/29282

PCT Pub. Date: Jun. 17, 1999

(30) Foreign Application Priority Data

Dec. 5, 1997 (DE) .......................................... 197 53 962

(51) Int. Cl.[7] .............................................. B32B 29/00
(52) U.S. Cl. ................... 428/537.5; 428/34.2; 428/532; 428/536; 424/70.2; 424/70.22; 424/70.27
(58) Field of Search ................................ 428/532, 536, 428/537.5, 34.2; 424/70.2, 70.22, 70.27

(56) References Cited

U.S. PATENT DOCUMENTS 5,830,487 A  11/1998  Klofta ........................ 424/402

FOREIGN PATENT DOCUMENTS

| DE | 1 492 007 | 10/1969 |
| DE | 33 11 292 A1 | 10/1984 |
| DE | 42 36 726 A1 | 5/1994 |
| WO | 97/09028 | 3/1997 |
| WO | WO 97/46205 | * 12/1997 |

* cited by examiner

Primary Examiner—Leszek Kiliman
(74) Attorney, Agent, or Firm—Michael J. Striker

(57) ABSTRACT

The permanent shaping method avoids overcurling of hair tips. Prior to performing the permanent shaping of the hair, the hair tips are protected by wrapping the hair tips with an impregnated foil and then performing the permanent shaping of the hair. The foil is an impregnated hair-tip paper that has been treated with an aqueous preparation that provides superior permanent shaping results. This aqueous preparation contains water, from 20 to 70 percent by weight of at least one lipophilic substance; from 1 to 25 percent by weight of at least one emulsifier and from 0.5 to 15 percent by weight of at least one organic acid. An impregnated foil made from silk or rice paper is also described.

20 Claims, No Drawings

FOIL FOR WRAPPING HAIR ENDS

The invention relates to an impregnated foil for wrapping the tips of hair (hair-tip paper) for use before permanent wave treatment in hair-care establishments.

To produce a permanent deformation of human hair, curlers are needed in addition to a reducing and oxidizing agent. The hair is rolled up along its longitudinal axis from the hair tips to the root region near the scalp. By the multiple wrapping of the hair around the roller, the hair tips necessarily assume a smaller curl than the hair in the root region. The small-curl tip deformation, however, presents a hindrance to the hairstyling and is therefore undesirable. A complicating factor is that the hair in the undamaged (original) state of the root region still has a more closed cuticle. For this reason, the root region is more resistant compared to the tip region which is months older and as a result of combing, washing, bleaching, dyeing or waving and of environmental influences gradually becomes more and more brittle and porous.

The aforeindicated drawbacks concerning the hair tips cause the hair's structure and ability to be styled to deteriorate.

Repeated attempts have been made to achieve uniform waving results and a tip protection/structure balance by means of permanent-wave pretreatment agents (see, for example, WO-A 97/09028) or by means of hair-tip paper impregnated with acids (see, for example, DE-A 33 11 292 and DE-A 1 492 007) or with oils (see, for example, DE-A 42 36 726). Permanent-wave pretreatment agents are sold as liquids or gels. It has been found in practice that application and dosing problems cannot be avoided with either of the two forms of consistency. A hair-tip paper impregnated only with acids or only with oils shows low efficacy in terms of wave and structure balance.

The object of the present invention is to avoid the aforesaid overcurling effect by means of a new foil so that during the period of exposure to the waving preparation the effect on the lengths and tips is gentle compared to that of the current methods, the known drawbacks thus being avoided. As a result, the hair structure is less damaged, and despite tighter winding the lengths and tips are given a comparable wave radius, like that in the root region near the scalp.

Surprisingly, we have now found that by use of a foil for hair-tip wrapping which has been impregnated with an aqueous preparation containing a) from 20 to 70 wt % of a lipophilic substance, b) from 1 to 25 wt % of an emulsifier and c) from 0.5 to 15 wt % of an organic acid it is possible to prevent the undesirable, too small-curled waving at the hair tips. At-the same time, the sensitive part of the hair is protected by the natural oils, and the acids prevent excessive swelling.

Foils such as hair-tip paper for permanent waving are in themselves known. They usually consist of wet-strength paper, for example long-fiber, silk or rice paper. However, the foil can also consist of some other absorbent material, for example of nonwoven material, cotton fabric or mixed fabrics of synthetic and natural fibers.

The lipophilic substance is preferably contained in the aqueous preparation in an amount from 40 to 60 wt %. Said substance is preferably a natural oil or wax selected from among physiologically well tolerated, particularly unsaturated, natural, hydrophobic oils or waxes. Particularly preferred is a vegetable oil such as, for example, jojoba oil, avocado oil, sunflower oil, wheat germ oil, peach kernel oil, mink oil, castor oil, sesame oil, peanut oil, rape oil, cottonseed oil or soybean oil. Other suitable physiologically well tolerated natural oils and waxes are montan wax, ozocerite, vaseline and paraffin or synthetic oils, such as, for example, silicone oils.

Preferably, the emulsifier is contained in the aqueous preparation in an amount from 2 to 15 wt % and particularly from 3 to 10 wt %. Said emulsifier is preferably selected from among compounds of the following group ethoxylated with 2 to 200 ethylene oxide units: fatty acids, fatty amides, fatty amines or fatty alcohols, each with 6 to 30 carbon atoms, and fatty esters with 6 to 30 carbon atoms in the fatty acid radical. Hydrogenated castor oil ethoxylated with, for example, 7 ethylene oxide units (for example, Arlacel® 989 supplied by ICI) and hydrogenated castor oil ethoxylated with 40 ethylene oxide units (for example, Cremophor® RH40, supplied by BASF) are particularly well suited emulsifiers.

Preferably, the organic acid is contained in the aqueous preparation in an amount from 1 to 7 wt % and particularly from 2 to 6 wt %. Said acid is preferably a hydroxycarboxylic acid or an aldehyde carboxylic acid or ketocarboxylic acid. Examples of suitable acids are glyoxylic, citric, ascorbic, lactic, tartaric, acetic, aconitic, acetylenedicarboxylic, ethylenedicarboxylic, ethylenemaleic, α-ethylcrotonic, i-amylmaleic, angelic, n-butylfumaric, n-butyl- or isobutylmaleic, citraconic, crotonic, fumaric, trans-glutaconic, isopropylmaleic, itaconic, maleic, mesaconic, a-methylitaconic, cis-α-methylglutaconic, trans-α-methylglutaconic, propiolic and cinnamic acid.

The aqueous preparation preferably contains from 30 to 60 wt % of water. In addition, it can optionally contain additives, such as stabilizers, buffers, fragrance oils, dyes as well as hair-conditioning and hair-care constituents such as, for example, cationic polymers, lanolin derivatives, cholesterol, pantothenic acid and betaine.

Said constituents are used in amounts usually employed for such purposes, the fragrance oils and dyes, for example, in amounts from 0.01 to 1 wt %, the buffers in a total amount from 0.1 to 10 wt %, the stabilizers and the hair-conditioners and hair-care agentin an amount from 0.1 to 5 wt % each.

Comparative tests on subjects for whom the hair-tip paper was impregnated only with oils or only with acids gave clearly poorer and unsatisfactory results. Thus, these tests confirm very impressively the above-described action.

EXAMPLES

Example 1

One part by weight of a 5% aqueous solution of glyoxylic acid was thoroughly mixed with one part by weight of a mixture of 84 wt % of jojoba oil and 16 wt % of a hydrogenated castor oil polyethoxylated with 40 ethylene oxide units (Cremophor® RH, supplied by BASF) to form an emulsion.

The resulting emulsion had the following composition:

| | |
|---|---|
| 2.5 wt % | of glyoxylic acid |
| 44.0 wt % | of jojoba oil |
| 8.0 wt % | of hydrogenated castor oil polyethoxylated with 40 ethylene oxide units (Cremophor ®, supplied by BASF) |

| | |
|---|---|
| 45.5 wt % | of water |

100.0 wt %

Conventional permanent-wave hair-tip paper was thoroughly impregnated with this emulsion, excess emulsion was removed, and the remaining emulsion was partly dried. The use of the slightly "moist" permanent-wave hair-tip paper thus obtained produced a very gentle effect on the hair tips which resulted in a long-lasting, soft hair wave.

Example 2

One part by weight of a 5% aqueous solution of lactic acid was thoroughly mixed with one part by weight of a mixture of 90 wt % of avocado oil and 10 wt % of a hydrogenated castor oil polyethoxylated with 40 ethylene oxide units (Cremophor® RH, supplied by BASF) to form an emulsion.

The resulting emulsion had the following composition:

| | |
|---|---|
| 2.5 wt % | of lactic acid |
| 45.0 wt % | of avocado oil |
| 5.0 wt % | of hydrogenated castor oil polyethoxylated with 40 ethylene oxide units (Cremophor ®, supplied by BASF) |
| 47.5 wt % | of water |

100.0 wt %

Conventional permanent-wave hair-tip paper was thoroughly impregnated with this emulsion, excess emulsion was removed, and the remaining emulsion was partly dried. The use of the slightly "moist" permanent-wave hair-tip paper thus obtained produced a very gentle effect on the hair tips which resulted in a long-lasting, soft hair wave.

Example 3

One part by weight of a 3 wt % aqueous solution of citric acid was mixed with one part by weight of a mixture of

| | |
|---|---|
| 33.0 wt % | of Buxus chinensis (jojoba oil) |
| 32.0 wt % | of Helianthus annuus (sunflower oil) |
| 31.0 wt % | of Persea gratissima (avocado oil) |
| 2.0 wt % | of hydrogenated castor oil ethoxylated with 40 ethylene oxide units (Cremophor ® RH40, supplied by BASF) |
| 1.0 wt % | of hydrogenated castor oil ethoxylated with 7 ethylene oxide units (Arlacel ® 989, supplied by ICI) |
| 0.1% | of antioxidants |
| 0.9 wt % | of water |

100.0 wt %

This gave an emulsion having the following composition:

| | |
|---|---|
| 16.50 wt % | of Buxus chinensis (jojoba oil) |
| 16.00 wt % | of Helianthus annuus (sunflower oil) |
| 15.50 wt % | of Persea gratissima (avocado oil) |
| 1.00 wt % | of hydrogenated castor oil ethoxylated with 40 ethylene oxide units (Cremophor ® RH40, supplied by BASF) |
| 0.50 wt % | of hydrogenated castor oil ethoxylated with 7 ethylene oxide units (Arlacel ® 989, supplied by ICI) |
| 1.50 wt % | of citric acid |
| 0.05 wt % | of antioxidants |
| 48.95 wt % | of water |

100.00 wt %

Conventional permanent-wave hair-tip paper was thoroughly impregnated with this emulsion, excess emulsion was removed, and the remaining emulsion was partly dried. The use of the slightly "moist" permanent-wave hair-tip paper thus obtained produced a very gentle effect on the hair tips which resulted in a long-lasting, soft hair wave.

What is claimed is:

1. An impregnated foil for wrapping hair tips during a permanent shaping treatment to protect the hair tips, wherein said impregnated foil comprises paper impregnated with an aqueous preparation, wherein said aqueous preparation contains from 30 to 60 percent by weight of water, from 20 to 70 percent by weight of at least one lipophilic substance; from 1 to 25 percent by weight of at least one emulsifier and from 0.5 to 15 percent by weight of at least one organic acid.

2. The impregnated toil as defined in claim 1, wherein said aqueous preparation contains from 1 to 7 percent by weight of said at least one organic acid, from 2 to 15 percent by weight of said at least one emulsifier and from 40 to 60 percent by weight of said at least one lipophilic substance.

3. The impregnated foil as defined in claim 1, wherein said at least one lipophilic substance is selected from the group consisting of jojoba oil, avocado oil, sunflower oil, wheat germ oil, peach kernel oil, mink oil, soybean oil, castor oil, sesame oil, peanut oil, rape seed oil, cotton seed oil, montan wax, ozocerite, petrolatum, physiologically well-tolerated paraffin oils and physiologically well-tolerated synthetic oils.

4. The Impregnated foil as defined in claim 1, wherein said at least one emulsifier is selected from the group consisting of fatty acids having 6 to 30 carbon atoms and ethoxylated with 2 to 200 ethylene oxide units, fatty amides having 6 to 30 carbon atoms and ethoxylated with 2 to 200 ethylene oxide units, fatty amines having 6 to 30 carbon atoms and ethoxylated with 2 to 200 ethylene oxide units, fatty alcohols having 6 to 30 carbon atoms and ethoxylated with 2 to 200 ethylene oxide units and fatty esters containing a fatty acid radical having 6 to 30 carbon atoms and ethoxylated with 2 to 200 ethylene oxide units.

5. The impregnated foil as defined in claim 1, wherein said at least one emulsifier is selected from the group consisting of hydrogenated castor oil ethoxylated with seven ethylene oxide units and hydrogenated castor oil hydrogenated with 40 ethylene oxide units.

6. The impregnated foil as defined in claim 1, wherein said paper is silk paper or rice paper.

7. The impregnated foil as defined in claim 1 and made by thoroughly impregnating or saturating said paper with said aqueous preparation and then removing excess amounts of said aqueous preparation.

8. The impregnated foil as defined in claim 1, wherein said aqueous preparation contains at least one additive ingredient selected from the group consisting of antioxidants, stabilizers, buffers, fragrance oils, cationic polymers, lanolin derivatives, cholesterol, pantothenic acid and betaine.

9. A method of permanent shaping hair that avoids over-curling hair tips, said method comprising the steps of:

a) providing an impregnated foil for wrapping hair tips, wherein said impregnated foil is impregnated with an aqueous preparation comprising from 20 to 70 percent by weight of at least one lipophilic substance; from 1 to 25 percent by weight of at least one emulsifier and from 0.5 to 15 percent by weight of at least one organic acid;

b) prior to performing the permanent shaping of the hair, protecting the hair tips of the hair to be permanently shaped by wrapping the hair tips with said impregnated foil;

c) after the protecting of the hair tips, performing the permanent shaping by treating the hair with a reducing agent used for permanent shaping, wrapping the hair on curlers and subsequently treating the hair with an oxidizing agent.

10. The method as defined in claim 9, wherein said aqueous preparation contains from 40 to 60 percent by weight of said at least one lipophilic substance.

11. The method as defined in claim 9, wherein said at least one lipophilic substance is a physiologically well-tolerated natural oil or wax.

12. The method as defined in claim 9, wherein said at least one lipophilic substance is selected from the group consisting of jojoba oil, avocado oil, sunflower oil, wheat germ oil, peach kernel oil, mink oil, soybean oil, castor oil, sesame oil, peanut oil, rape seed oil, cotton seed oil, montan wax, ozocerite, petrolatum, physiologically well-tolerated paraffin oils and physiologically well-tolerated synthetic oils.

13. The method as defined in claim 9, wherein said at least one lipophilic substance consists of silicone oil.

14. The method as defined in claim 9, wherein said aqueous preparation contains from 2 to 15 percent by weight of said at least one emulsifier.

15. The method as defined in claim 9, wherein said at least one emulsifier is selected from the group consisting of fatty acids having 6 to 30 carbon atoms and ethoxylated with 2 to 200 ethylene oxide units, fatty amides having 6 to 30 carbon atoms and ethoxylated with 2 to 200 ethylene oxide units, fatty amines having 6 to 30 carbon atoms and ethoxylated with 2 to 200 ethylene oxide units, fatty alcohols having 6 to 30 carbon atoms and ethoxylated with 2 to 200 ethylene oxide units and fatty esters containing a fatty acid radical having 6 to 30 carbon atoms and ethoxylated with 2 to 200 ethylene oxide units.

16. The method as defined in claim 9, wherein said at least one emulsifier is selected from the group consisting of hydrogenated castor oil ethoxylated with seven ethylene oxide units and hydrogenated castor oil hydrogenated with 40 ethylene oxide units.

17. The method as defined in claim 9, wherein said aqueous preparation contains from 1 to 7 percent by weight of said at least one organic acid.

18. The method as defined in claim 9, wherein said at least one organic acid is selected from the group consisting of glyoxylic acid, citric acid, ascorbic acid, lactic acid, tartaric acid, acetic acid, aconitic acid, acetylene-dicarboxlic acid, ethylenedicarboxylic acid, ethylenemaleic acid, $\alpha$-ethylcrotonic acid, i-amylmaleic acid, angelic acid, n-butyifumaric acid, n-butylmaleic acid, isobutylmaleic acid, citraconic acid, crotonic acid, fumaric acid, trans-glutaconio acid, isopropylmaleic acid, itaconic acid, maleic acid, mesaconolc acid, o-methylitaconic acid, cis-$\alpha$-methylglutaconic acid, trans-$\alpha$-methylglutaconic acid, propiolic acid and cinnamic acid.

19. The method as defined in claim 9, wherein said foil comprises paper.

20. The method as defined in claim 19, wherein said paper is silk paper having wet-strength or rice paper having wet-strength.

* * * * *